United States Patent [19]

Schroeppel et al.

[11] Patent Number: 5,749,900
[45] Date of Patent: May 12, 1998

[54] IMPLANTABLE MEDICAL DEVICE RESPONSIVE TO HEART RATE VARIABILITY ANALYSIS

[75] Inventors: Edward A. Schroeppel; David Prutchi; André G. Routh, all of Lake Jackson, Tex.

[73] Assignee: Sulzer Intermedics Inc., Angleton, Tex.

[21] Appl. No.: 570,727

[22] Filed: Dec. 11, 1995

[51] Int. Cl.$^6$ ............................................. A61N 1/365
[52] U.S. Cl. ............................................................. 607/4
[58] Field of Search ................................. 607/4, 5, 6, 17, 607/25

[56] References Cited

U.S. PATENT DOCUMENTS

| | | | |
|---|---|---|---|
| 4,404,972 | 9/1983 | Gordon et al. | 128/419 |
| 4,539,992 | 9/1985 | Calfee et al. | 128/419 |
| 4,830,006 | 5/1989 | Haluska et al. | 128/419 |
| 4,832,038 | 5/1989 | Arai et al. | 128/670 |
| 4,862,361 | 8/1989 | Gordon et al. | 364/413.06 |
| 4,895,151 | 1/1990 | Grevis | 607/6 |
| 5,002,052 | 3/1991 | Haluska | 128/419 |
| 5,107,850 | 4/1992 | Olive | 607/4 |
| 5,156,148 | 10/1992 | Cohen | 607/4 |
| 5,201,321 | 4/1993 | Fulton | 128/702 |
| 5,312,452 | 5/1994 | Salo | 607/17 |
| 5,342,401 | 8/1994 | Spano et al. | 607/5 |
| 5,350,412 | 9/1994 | Hoegnelid et al. | 607/34 |
| 5,354,317 | 10/1994 | Alt | 607/19 |
| 5,370,666 | 12/1994 | Lidberg et al. | 607/16 |
| 5,431,685 | 7/1995 | Alt | 607/6 |
| 5,437,285 | 8/1995 | Verrier et al. | 128/702 |
| 5,458,620 | 10/1995 | Adams et al. | 607/5 |
| 5,466,245 | 11/1995 | Spinelli et al. | 607/17 |

FOREIGN PATENT DOCUMENTS 1683679  10/1991  U.S.S.R. .

OTHER PUBLICATIONS

K. Airaksinen, "Impaired Vagal Heart Rate Control in Coronary Artery Disease," *Br Heart J.*, (1987), vol. 58, pp. 592–597.

S. Akselrod, et al., "Power Spectrum Analysis of Heart Rate Fluctuation: A Quantitative Probe of Beat-to-Beat Cardiovascular Control," (1981). *AAAS*, (1981), vol. 213, pp. 222–222.

M. Alcalay, "Paradoxical Pharmacodynamic Effect of Atropine on Parasympathetic Control: A Study by Spectral Analysis of Heart Rate Fluctuations," *Clin Pharacol Ther,* (1992), vol. 52, No. 5, pp. 518–527.

C. Alli, "Prevalence and Variability of Orthostatic Hypotension in the Elderly. Results of the 'Italian Study on Blood Pressure in the Elderly (SPAA)'," *The European Society of Cardiology, European Heart Journal,* (1992), vol. 13, pp. 178–182.

M. Appel, "Beat to Beat Variability in Cardiovascular Variables: Noise or Music?", *The American College of Cardiology,* (1989), JACC, vol. 14, No. 5, pp. 1139–1148.

Y. Arai, "Modulation of Cardiac Autonomic Activity During and Immediately After Exercise," *The American Physiological Society,* (1989), Heart Rate Power Spectrum in Exercise, pp. 132–141.

(List continued on next page.)

*Primary Examiner*—William E. Kamm
*Attorney, Agent, or Firm*—John R. Merkling

[57] ABSTRACT

A method and apparatus for evaluating heart rate variability of the heart of a person in order to forecast a cardiac event. A cardiac stimulator receives heart beat signals from the heart and determines a measurement of heart rate variability based on statistical data derived from the heart beat signals and sensing data derived from a sensor. This measurement of heart rate variability is compared with previously stored heart rate variability zones defining normal and abnormal heart rate variability. These zones are modifiable after the occurrence of a cardiac event. Once a cardiac event is detected, a pathway is computed which extends from a generally normal heart rate variability condition to an abnormal heart rate variability condition. Subsequent measurements of heart rate variability are compared with this pathway. Selective therapy regimes are initiated depending on the measurement of heart rate variability.

5 Claims, 7 Drawing Sheets

OTHER PUBLICATIONS

M. Stramba-Badiale, "Sympathetic-Parasympathetic Interaction and Accentuated Antagonism Conscious In Dogs," *The American Physiological Society*, (1991), pp. 335–340.

J. Bassingwaighte, "Chaos in Cardiac Signals" Interactive Phenomena in the Cardiac System, (1993) Chap. 20, pp. 207–218.

J. Bigger, "Time Course of Recovery of Heart Period Variability After Myocardial Infarction", *The American College of Cardiology*, JACC, (1991), vol. 18, No. 7, pp. 1643–1649.

J. Bigger, "Components of Heart Rate Variability Measured During Healing of Acute Myocardial Infarction," *The American Journal of Cardiology*, (1988), vol. 61, pp. 208–215.

J. Bigger, "Frequency Domain Measures of Heart Period Variability and Mortality After Myocardial Infarction," *Circulation*, (1992), vol. 85, No. 1, pp. 164–171.

G. Billman, "Time–Series Analysis of Heart Rate Variability During Submaximal Exercise," *Circulation*, (1989) vol. 80, No. 1, pp. 146–157.

T. Binder, "Prognostic Value of Heart Rate Variability in Patients Awaiting Cardiac Transplantation," *Pace*, (1992), vol. 15, Part II, pp. 2215–2220.

E. Kristal–Boneh, "Heart Rate Variability in Health and Disease," *Scnd J Work Environ Health*, (1995), vol. 21, No. 2, pp. 85–95.

J. Carter, Jr., "Torsade De Pointes Complicating Acute Myocardial Infarction: The Importance of Autonomic Dysfunction as Assessed by Heart Rate Variability," *Clin. Cardiol.*, (1992), vol. 15, pp. 769–772.

G. Casolo, "Decreased Spontaneous Heart Rate Variability in Congestive Heart Failure," *The American Journal of Cardiology*, (1989), vol. 64, pp. 1162–1167.

G. Cornelissen, "From Various Kinds of Heart Rate Variability to Chronocardiology," *The American Journal of Cardiology*, (Oct. 1990), pp. 863–868.

P. Coumel, "Modifications of Heart Rate Variability Preceding the Onset of Tachyarrhythmias," *Cardiologia*, (1990), vol. 35, Suppl al n 1), pp. 7–12.

P. Coumel, "Heart Rate Variability in Left Ventricular Hypertrophy and Heart Failure, and the Effects of Beta–blockade," *European Heart Journal*, (1991), vol. 12, pp. 412–422.

P. Counihan, "Assessment of Heart Rate Variability in Hypertrophic Cardiomyopathy," *Circulation*, (1993), vol. 88, No. 4, part 1, pp. 1682–1690.

M. Cowan, "Power Spectral Analysis of Heart Rate Variability After Biofeedback Training," *Journal Electrocardiology*, vol. 23, pp. 85–94.

W. Craelius, "Heart Rate Variability as an Index of Autonomic Imbalance in Patients with Recent Myocardial Infarction," *Medical Biological Engineering & Computing*, (1992), pp. 385–388.

T. Cripps, "Prognostic Value of Reduced Heart Rate Variability After Myocardial Infarction: Clinical Evaluation of a New Analysis Method," *Br Heart J*, (1991), vol. 65, pp. 14–19.

R. DeBoer, "Communications," *IEEE Transactions on Biomedical Engineering*, (Apr. 1984), vol. BME–31, No. 4, pp. 384–387.

G. De Ferrari, "Pharmacologic Modulation of the Autonomic Nervous System in the Prevention of Sudden Death." *The American College of Cardiology*, (1993) JACC vol. 22, No. 1, pp. 283–290.

A. Dritsas, "Beat–to–Beat Variability in Stroke volume During VVI Pacing as Predictor of Hemodynamic Benefit From DDD Pacing," *Pace* (Aug. 1993), vol. 16, pp. 1713–1718.

F. Estafanous, "Analysis of Heart Variability to Assess Hemodynamic Alterations Following Induction of Anesthesia," *Journal of Cardiothoracic and Vascular Anesthesia*, (1992), vol. 6, No. 6, pp. 651–657.

T. Farrell, "Prognostic Value of Baroreflex Sensitivity Testing After Acute Myocardial Infarction," *Br Heart J*, (1992), vol. 67, pp. 129–137.

R. Farrell, "Risk Stratification for Arrhythmic Events in Postinfarction Patients Based on Heart Rate Variability, Ambulatory Electrocardiographic Variables and the Signal–Averaged Electrocardiogram," *The American College of Cardiology*, JACC, (1991), vol. 18, No. 3, pp. 687–697.

J. Fleiss, "The Correlation Between Heart Period Variability and Mean Period Length," *Statistics In Medicine*, (1992), vol. 11, pp. 125–129.

R. Freeman, "Spectral Analysis of Heart Rate in Diabetic Autonomic Neuropathy," *Arch Neurol*, (Feb. 1991), vol. 48, pp. 185–190.

R. Furlan, "Continuous 24–hour Assessment of the Neural Regulation of Systemic Arterial Pressure and RR Variabilities in Ambulant subjects," *Circulation*, (1990), vol. 81, No. 2, pp. 537–547.

C. Garrard, "Spectral Analysis of Heart Rate Variability in the Sepsis Syndrome," *Clinical Autonomic Research*, (1993), vol. 3, pp. 5–13.

R. Goldsmith, "Comparison of 24–Hour Parasympathetic Activity in Endurance Trained and Untrained Young Men," *J Am Coll Cardiol*, (1992), vol. 20, pp. 552–558.

B. Golosarsky, Detection of Abnormal and Induction of Normal Heart Rate Variability, pp. 1–72.

J. Gomes "Identification of Patients with High Risk of Arrhythmic Mortality," *Cardiology Clinics*, (1993), vol. 11, No. 1, pp. 55–63.

D. Gordon, "Heart–Rate Spectral Analysis: A Noninvasive Probe of Cardiovascular Regulation in Critically Ill Children with Heart Disease," *Pediatric Cardiology*, (1988), vol. 9, pp. 69–77.

P. Grossman, "Prediction of Tonic Parasympathetic Cardiac Control Using Respiratory Sinus Arrhythmia: The Need for Respiratory Control," *Psychophysiology*, (1991), vol. 28, No. 2, pp. 201–216.

H. Huikuri, "Circadian Rhythms of Frequency Domain Measures of Heart Rate Variability in Healthy Subjects and Patients With Coronary Artery Disease," *Circulation*, (1994), vol. 90, No. 1, pp. 121–126.

J. Jennings, "Does Aging Differentially Reduce Heart Rate Variability Related to Respiration?," *Experimental Aging Research*, (1984), vol. 10, No. 1, pp. 19–23.

J. Kanters, "Lack of Evidence for Low–Dimensional Chaos in Heart Rate Variability," *J. Cardiovasc Electrophysiol*, (1994), vol. 5, pp. 591–601.

D. Kaplan, "The Analysis of Variability," *J. Cardiovasc Electrophysiol*, (1994), vol. 5, pp. 16–19.

J. Karin, "An Estimate of Fetal Autonomic State by Spectral Analysis of Fetal Heart Rate Fluctuations," *Pediatric Research*, (1993), vol. 34, No. 2, pp. 134–138.

P. Katona, "Respiratory Sinus Arrhythmia: Noninvasive Measure of Parasympathetic Cardiac Control," *Journal Of Applied Physiology*, (1975), vol. 39, No. 5, pp. 801–805.

M. Kienzle, "Clinical, Hemodynamic and Sympathetic Neural Correlates of Heart Rate Variability in Congestive Heart Failure," *Am J. Cardiol*, (1992), vol. 69, pp. 761–767.

R. Kleiger, "Decreased Heart Rate Variability and Its Association with Increased Mortality After Acute Myocardial Infarction," *Am J cardiol*, (1987), vol. 59, pp. 256–262.

T. Latson, "Effects of Surgical Stimulation on Autonomic Reflex Function: Assessment by Changes in Heart Rate Variability," *British Journal of Anesthesia*, (1993), vol. 70, pp. 301–305.

C. Leffler, "Rate–Related and Autonomic Effects on Atrioventricular Conduction Assessed Through Beat–to–Beat PR Interval and Cycle Length Variability," *J Cardiovasc Electrophysiol*, (1994), vol. 5, pp. 2–15.

N. Lippman, "Nonlinear Predictive Interpolation," *Journal of Electrocardiology, Supplement*, vol. 26, pp. 14–19.

M. Lishner, "Spectral Analysis of Heart Rate Fluctuations. A Non–invasive, Sensitive Method for the Early Diagnosis of Autonomic Neuropathy in Diabetes Mellitus," *Journal of the Autonomic Nervous System*, (1987), vol. 19, pp. 119–125.

C. Maayan, "Evaluation of Autonomic Dysfunction in Familial Dysautonomia by Power Spectral Analysis," *Journal of the Autonomic Nervous System*, (1987), vol. 21, pp. 51–58.

M. Malik, "Electrophysiology, Pacing, and Arrhythmia," Clin. Cardiol., (1990), vol. 13, pp. 570–576.

M. Malik, "Heart Rate Variability: From Facts to Fancies*," *Journal of the American College of Cardiology*, (1993), vol. 22, No. 2, pp. 566–568.

M. Malik, "Significance of Long Term Components of Heart Rate Variability for the Further Prognosis After Acute Myocardial Infarction," (1990), vol. 24, pp. 793–803.

A. Malliani, "Power Spectral Analysis of Cardiovascular Variability in Patients at Risk for Sudden Cardiac Death," *J Cardiovasc Electrophysiol*, (1994), vol. 5, pp.274–286.

G. Mancia, "Blood Pressure and heart Rate Variabilities in Normotensive and Hypertensive Human Beings," *Circulation Research*, (1983), vol. 53, No. 1, pp. 96–104.

G. Moody, "Derivation of Respiratory Signals From Multi-Lead ECGS," *IEEE*, (1985), pp. 113–116.

M. Moser, "Heart Rate Variability as a Prognostic Tool in Cardiology," Circulation, (1994), vol. 90, pp. 1078–1082.

J. Muller, "Circadian Variation and Triggers of Onset of Acute Cardiovascular Disease," *Circulation*, (1989), vol. 79, No. 4, pp. 733–743.

J. Nolan, "Decreased Cardiac Parasympathetic Activity in Chronic Heart Failure and Its Relations to Left Ventricular Function," *Br Heart J*, (1992) Vo. 67, pp. 482–485.

T. Nonnenmacher, "Fractal Landscapes in Physiology & Medicine: Long–Range Correlations in DNA Sequences and Heart Rate Intervals," appearing in *Fractuals in Biology and Medicine*, (1994), pp. 56–65.

O. Odemuyiwa, "Temporal Influences on the Prediction of Postinfarction Mortality by Heart Rate Variability: A Comparison with the Left Ventricular Ejection Fraction," *Br Heart J*, (1994), vol. 71, pp. 521–527.

O. Odemuyiwa, "Influences of Age on the Relation Between Heart Rate Variability, Left Ventricular Ejection Fraction, Frequency of Ventricular Extrasystoles, and Sudden Death After Myocardial Infarction," *Br Heart J*, (1992), vol. 67, pp. 521–527.

O. Odemuyiwa, "Multifactorial Prediction of Arrhythmic Events After Myocardial Infarction. Combination of Heart Rate Variability and Left Ventricular Ejection Fraction with Other Variables," *Pace*, (1991), vol. 4, Part II, pp. 1986–1991.

O. Odemuyiwa, "Comparison of the Predictive Characteristics of Heart Rate Variability Index and Left Ventricular Ejection Fraction for All–Cause Mortality, Arrhythmic Events and Sudden Death After Acute Myocardial Infarction," *The American journal of Cardiology*, (1991), vol. 68, pp. 434–439.

R. Pedretti, "Effect of Thrombolysis on Heart Rate Variability and Life–Threatening Ventricular Arrhythmias in Survivors of Acute Myocardial Infarction," *The Journal of College of Cardiology*, (1994), vol. 23, No. 1, pp. 19–26.

C. Peng, "Long–Range Anticorrelations and Non–Gaussian Behavior of the Heartbeat," *Physical Review Letters*, (1990), vol. 70, No. 9, pp. 1343–1346.

C. Peng, "Quantification of Scaling Exponents and Crossover Phenomena in Nonstationary Heartbeat Time Series," pp. 1–11.

R. Perini, "The Influence of Exercise Intensity on the Power Spectrum of Heart Rate Variability," *European journal of Applied Physiology*, (1990), vol. 61, pp. 143–148.

F. Perticone, "Heart Rate Variability and Sudden Infant Death Syndrome," *Pace*, (1990), vol. 13, Part II, pp. 2096–2099.

B. Pomeranz, "Assessment of Autonomic Function in Humans by Heart Rate Spectral Analysis," *The American Journal of Physiology*, (1985), pp. 151–153.

S. Ryan, "Gender–and Age–Related Differences in Heart Rate Dynamics: Are Women More Complex Than Men?," *The Journal of American College of Cardiology*, (1994), vol. 24, No. 7, pp. 1700–1707.

J. Saul, "Transfer Function Analysis of the Circulation: Unique insights into Cardiovascular Regulation," *The American Journal of Physiology*, (1991), pp. 1231–1245.

J. Saul, "Heart Rate and Muscle Sympathetic Nerve Variability During Reflex Changes of Automatic Activity," *The American Journal of Physiology*, (1990), pp. 713–721.

J. Saul, "Analysis of Long Term Heart Rate Variability: Methods, 1/f Scaling and Implications," *IEEE*, (1988), pp. 419–422.

J. Saul, "Assessment of Autonomic Regulation in Chronic Congestive Heart Failure by Heart Rate Spectral Analysis," *The American Journal of Cardiology*, (1988), vol. 61, pp. 1292–1299.

B. McA Sayers, "Analysis of Heart Rate Variability," *Ergonomics*, (1973) vol. 16, No. 1, pp. 17–32.

P. Schwartz, "Autonomic Nervous System and Sudden Cardiac Death," *Circulation*, (1992), vol. 85, pp. 77–91.

J. Skinner, "Brain Mechanisms Underlying Fatal Cardiac Arrhythmias," *Neurocardiology*, (1993), vol. 11, No. 2, pp. 325–351.

K. Stein, "Prognostic Value and Physiological Correlates of Heart Rate Variability in Chronic Severe Mitral Regurgitation," *Circulation*, (1993), vol. 88, pp. 127–135.

B. Takase, "Heart Rate Variability in Patients With Diabetes Mellitus, Ischemic Heart Disease, and Congestive Heart Failure," *The Journal of Electrocardiology*, (1992), vol. 25, No. 2, pp. 79–88.

J. Triedman, "Mild Hypovolemic Stress Alters Autonomic Modulation of Heart Rate," *Hypertension*, (1993), vol. 21, pp. 236–247.

J. Valkama, "Relation Between Heart Rate Variability and Spontaneous and Induced Ventricular Arrhythmias in Patients with Coronary Artery Disease," *The Journal of American College of Cardiology*, (1995), vol. 25, pp. 437–443.

C. van Ravenswaaij, "Heart Rate Variability," *The Annuals of Internal Medicine*, (1993), vol. 118, pp. 436–447.

R. Wakai, "Spectral Analysis of Antepartum Fetal Heart Rate Variability From Fetal Magnetocardiogram Recordings," Early Human Development, (1993), vol. 35, pp. 5–24.

A. Watanabe, "The Role of the Autonomic Central Nervous System in Mediating and Modifying the Action of Cardiac Antiarrhythmic Drugs," *The Annals New Academy of Sciences*, pp. 90–102.

IMPLANTABLE MEDICAL DEVICE RESPONSIVE TO HEART RATE VARIABILITY ANALYSIS

BACKGROUND

Traditionally, human heartbeat was thought to be regulated according to classical principles of homeostasis. Under this theory, the human physiological system operates in a manner which adjusts heart rate variability to achieve a state of equilibrium. Clinicians, in fact, traditionally described the normal beat activity of the heart as a "regular or normal sinus rhythm."

Modern views now depart from these traditional ideologies. More recent studies and research show that, even with healthy individuals, the heart does not beat with metronomic regularity. Rather, the heart exhibits beat-to-beat fluctuations which are far from equilibrium. See C. K. Peng, et al, "Fractal Landscapes in Physiology & Medicine: Long-Range Correlations in DNA Sequences and Heart Rate Intervals" pp. 55–65, appearing in *Fractals in Biology and Medicine*, by T. F. Nonnenmacher, et. al (Ed.) (1994). Electrocardiograms, for example, show that an individual will exhibit a fluctuating or erratic heart rate variability during both rest and sleep periods.

Beat-to-beat fluctuations which occur around a person's mean heart rate are known as heart rate variability. The fluctuations from beat-to-beat are attributed, in part, to the nonlinear interaction between the sympathetic and parasympathetic branches of the involuntary nervous system. The sympathetic autonomic and parasympathetic autonomic nervous systems regulate, to some extent, the sinoatrial (SA) node and atrioventricular (AV) node of the heart and, thus, largely influence the control of the heart rate. These two nervous systems operate somewhat reciprocally to effect changes in the heart rate. In this regard, parasympathetic stimulation decreases the firing rate of the pacing cells located in the sinus node of the heart. Sympathetic stimulation, on the other hand, increases this firing rate.

Most clinicians agree that the parasympathetic and sympathetic inputs to the SA node mediate low frequency heart rate fluctuations (i.e., generally below 0.15 Hz), whereas modulation of parasympathetic outflow mediates higher frequency fluctuations. Studies have further shown that a decrease in heart rate variability correlates with a decrease in parasympathetic nervous activity and an accompanied increase in sympathetic nervous activity. See J. Thomas Bigger, et al, "Components of Heart Rate Variability Measured During Healing of Acute Myocardial Infarction" *American Journal of Cardiology*, Vol. 61 (1988), pp.208–215. In a healthy, resting heart, for instance, the parasympathetic activity dominates to maintain the heart rate. However, in an unhealthy heart, for example one having heart disease, sympathetic activity may more influence and control the heart rate.

Over the past several years, heart rate variability was increasingly recognized as a diagnostic and a prognostic indication of the cardiac health risks to which a person is susceptible. As a result, much research has been directed toward heart rate variability. In particular, clinicians have been investigating the possibility that heart rate variability may provide important information to forecast impending cardiac anomalies. One study, for example, verified that a low standard deviation of heart rate variability is a powerful prognostic indicator of sudden coronary death in patients recovering from acute myocardial infarction. See Alberto Malliani, et al, "Power Spectral Analysis of Cardiovascular Variability in Patients at Risk for Sudden Cardiac Death" *Journal of Cardiovascular Electrophysiology*, Vol. 5 (1994), pp. 274–286.

Today, cardiologists generally are in accord that heart rate variability does have a correlation to the present condition of a person's heart rate or the future occurrence of an abnormal cardiac event. In fact, numerous studies have been performed which demonstrate this correlation. For example, if the heart rate of a healthy individual is compared to the rate of a patient having congestive heart failure, distinct differences in the beat intervals will be observed. In this regard, the healthy individual will exhibit more complex patterns of fluctuation than the non-healthy individual.

Furthermore, studies specifically relate heart rate variability to death in cardiac patients. Diminished heart rate variability now is associated with an increased risk for ventricular fibrillation and sudden cardiac death. One study concluded:

> Heart rate variability is an independent predictor of death when other known postinfarction risk variables (for example, prolonged left ventricular ejection fraction, ventricular arrhythmias, and clinical variables) are considered. Heart rate variability has a higher association with risk for death than other variables obtained by Holter monitoring, (for example, mean heart rate and ventricular arrhythmias). Heart rate variability also appears to be a better predictor of arrhythmia complications than prolongation of the ejection fraction.

See Conny M. A. van Ravenswaaij-Arts, et al, *Annals of Internal Medicine*, Vol. 118 (1993), pp. 436–447.

As noted, clinicians use heart rate variability to predict the onset of sudden cardiac death. Although the exact cause of cardiac death is not completely understood, most victims suffer from ventricular tachycardia that degenerates into ventricular fibrillation. Investigators have exhausted significant effort to predict the onset and triggers for such ventricular tachyarrhythmias. Heart rate variability is one available predictive value. Recent studies in this field verify that a decrease or increase in heart rate variability during the first several weeks after an acute myocardial infarction may be used to predict subsequent mortality or ventricular rhythmic disorders. One study examined approximately 800 patients who had survived an acute myocardial infarction and concluded that patients with a heart rate variability of less than 50 milliseconds had a 5.3 times higher mortality rate than those patients with a heart rate variability of more than 100 milliseconds. See Robert E. Kleiger, et al, "Decreased Heart Rate Variability and Its Association with Increased Mortality After Acute Myocardial Infarction" *American Journal of Cardiology*, Vol. 59 (1987), pp. 256–262. Patients experiencing congestive heart failure and coronary artery disease also exhibit a decrease in heart rate variability. See Casolo G. et. al, "Decreased Spontaneous Heart Rate Variability in Congestive Heart Failure," *American Journal of Cardiology*, Vol. 64 (1989), pp. 1162–1167.

Even in healthy individuals having normal heart rate variability, the heart rate intervals generally have a circadian variation. This circadian variation, however, may begin to become less pronounced and more irregular several minutes to several hours before the onset of an abnormal cardiac event. Researchers, for example, have found that heart rate variability progressively decreases in the hours preceding the onset of arrhythmia. Monitoring heart rate variability in such instances thus provides clinicians with a tool to forecast impending cardiac events.

As one advantage, measurements of heart rate variability are generally non-invasive and may be reliably performed.

A Holter monitor or electrodes affixed to the patient measure heart rate very accurately. The electrodes detect the heartbeat, usually the R—R interval, for a series of beats. Thereafter, statistical data, such as mean, median, and standard deviation, are computed and then used to forecast the onset of a cardiac event. One known method for using heart rate variability is to compare heart rate intervals recorded under normal heart rate conditions to subsequent heart rate intervals. Deviations between the two recordings then may be used as an indication of heart rate variability fluctuation. In one embodiment, a Holter monitor records R—R intervals while the patient exhibits normal or healthy heart rate variability. An algorithm based on mean and standard deviation then computes a single user value which is stored in permanent memory. This user value represents the patient's stress state during normal heart rate variability conditions. Thereafter, the patient wears a wrist detector which monitors the R—R intervals for discrete beat periods, for example 100 beats. Once a beat period is complete, the wrist detector uses the algorithm to compute the patient's present user value or present stress state. This present user value is then compared to the permanently stored user value which was previously recorded under normal heart rate conditions. Theoretically, this comparison reveals deviations from normal heart rate variability which, in turn, are a measure of the patient's cardiac stress state. Large deviations between the two user values reflect large deviations in the autonomic nervous system balance between the sympathetic and parasympathetic activities. For example, if the presently recorded user value deviates from the permanently stored user value more than 25%, the patient may be subject to an elevated stress level with an accompanying abnormal heart rate variability.

One important disadvantage associated with methods and apparatus for utilizing heart rate variability concerns the failure to provide a more intelligent algorithmic structure. Heart rate variability algorithms typically first compute a present user value based on the R—R intervals. Thereafter, this present user value is compared with a previously stored user value and a deviation between the two is computed. The algorithmic structure itself, however, remains unchanged. Thus, when subsequent R—R intervals are received and new user values calculated, these values are again compared with the same permanently stored user value. As such, the algorithm repeatedly uses the same threshold parameters defining normal and abnormal heart rate variability.

Another disadvantage associated with methods and apparatus for utilizing heart rate variability concerns the treatment of heart rate variability data leading up to an abnormal cardiac event. Devices measuring heart rate variability often have memories which operate on a first-in-first-out basis. These types of memories hold the heart rate data in sequence and discard the oldest data and save the newest, incoming data. The older data, however, may provide important information regarding the onset of subsequent cardiac events.

SUMMARY

The present invention is addressed to a method and apparatus for evaluating heart rate variability of a person in order to recognize or forecast a cardiac event. Heart rate variability zones initially are established to define normal and abnormal cardiac sinus rhythm of the person. Thereafter, these zones are automatically modified after the occurrence or non-occurrence of a cardiac event. As such, the bounds defining normal and abnormal heart rate variability specifically adapt to a person's physiological and cardiological conditions. Once a cardiac event occurs, a pathway leading up to that event is stored. Patient heart rate variability is then compared to this pathway to determine the re-occurrence of a cardiac event.

In the present invention, a microprocessor-based cardiac stimulator receives heart-beat signals from the heart. The cardiac stimulator computes time intervals occurring between successive heart beats and then derives a measurement of heart rate variability from epoch data for predetermined time periods. This epoch data may include both statistical data derived from the time intervals and sensing data derived from patient sensors. The cardiac stimulator then compares measurement of heart rate variability with previously stored heart rate variability zones which define normal and abnormal heart rate variability. If the measurement of heart rate variability is within the limits of an abnormal heart rate variability zone then an appropriate therapy regime is initiated. On the other hand, if the measurement of heart rate variability is within a normal heart rate variability zone, a therapy regime is not initiated. However, when the measurement of heart rate variability is within a normal heart rate variability zone and the person is nevertheless experiencing a cardiac event, then the abnormal heart rate variability zone is modified to include the measurement of heart rate variability. As such, the definition of normal and abnormal heart rate variability changes to meet the cardiac requirements of a particular individual.

Once a cardiac event occurs, a memory permanently stores the present epoch data and, additionally, a series of epoch data leading up to the event. Together, this series of epoch data forms a pathway from a generally normal heart rate variability condition to an abnormal heart rate variability condition. This pathway aids in predicting the occurrence of future cardiac events and in identifying the occurrence of present cardiac events. In this regard, all measurements of heart rate variability occurring after the cardiac event are compared with the pathway. This comparison reveals whether the person is again experiencing conditions similar to those leading to the prior cardiac event.

As another advantage, the abnormal heart rate variability zone may be divided into a plurality of abnormal subzones. Each of these subzones corresponds to a therapy regime for initiating further sensing or therapeutic vigilance. Further, the therapy regimes may have a structure with progressively higher degrees of aggressiveness and vigilance.

Additionally, selective activation of therapy regimes minimizes non-essential energy consumptive and diagnostic activities and, thus, conserves power supply longevity.

The invention, accordingly, comprises the apparatus and method possessing the construction, combination of elements, and arrangement of parts which are exemplified in the following detailed description. For a fuller understanding of the nature and objects of the invention, reference should be made to the following detailed description taken in connection with the accompanying drawings.

DETAILED DESCRIPTION

Figure 1:
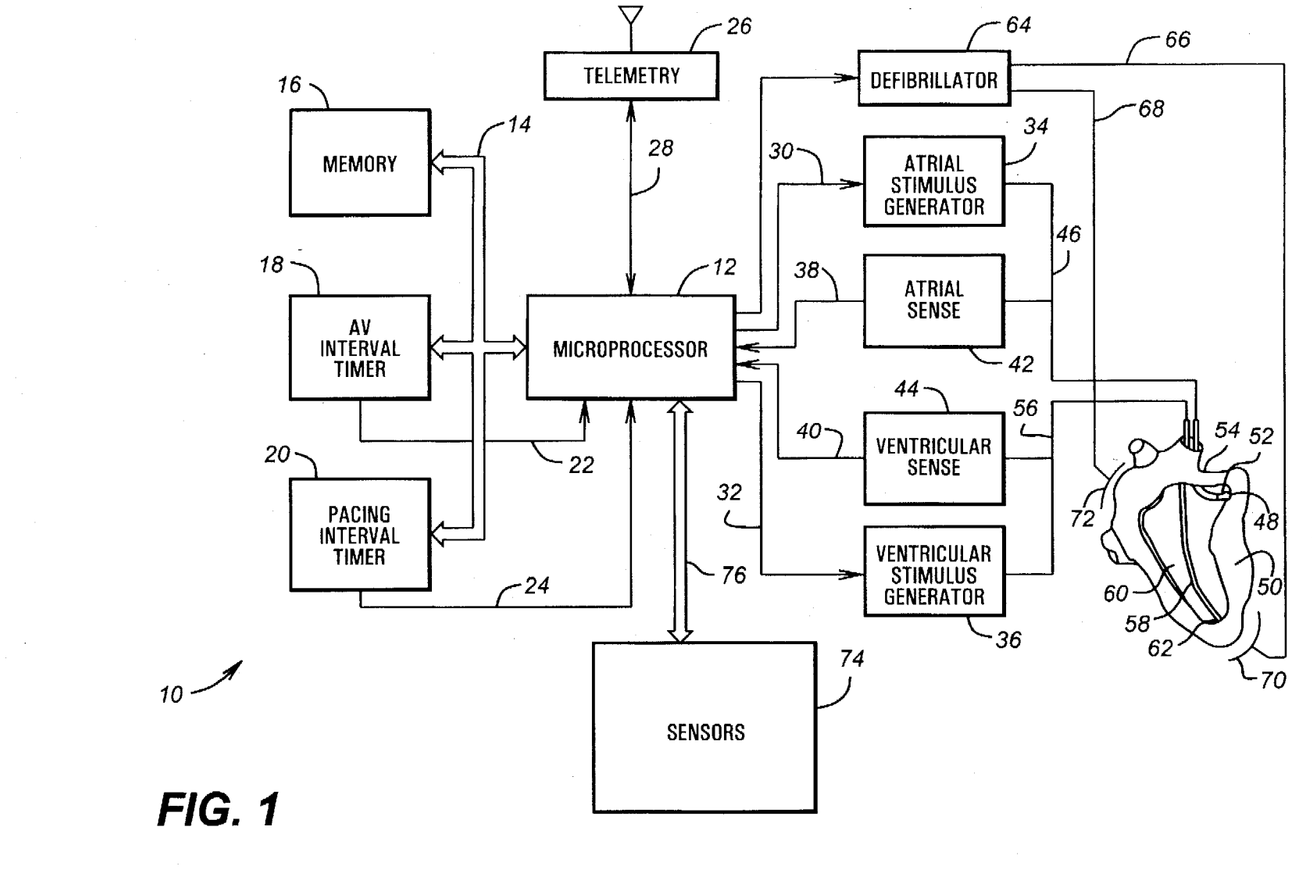
FIG. 1 is a block diagram of an implantable cardiac pulse stimulator.

FIG. 1 is a block diagram illustrating an implantable cardiac stimulator 10 for carrying out the teachings of the present invention. Stimulator 10 may be a pacemaker, defibrillator, or other implantable pulse generator. A microprocessor 12 provides control and computational facilities for stimulator 10. Microprocessor 12 has input/output ports connected in a conventional manner via bidirectional bus 14 to memory 16, an A–V interval timer 18, and a pacing interval timer 20. A–V interval timer 18 and pacing interval timer 20 have an output connected individually via lines 22 and 24, respectively, to a corresponding input port of microprocessor 12.

A–V and pacing interval timers 18 and 20 may be external to microprocessor 12, as illustrated, or internal thereto. Additionally, these timers may be conventional up/down counters of the type that are initially loaded with a count value and count up to or down from the value and output a roll-over bit upon completing the programmed count. The initial count value is loaded into A–V and pacing interval timers 18 and 20 on bus 14. Respective roll-over bits are output to microprocessor 12 on lines 22 and 24. Memory 16 preferably includes both ROM and RAM. Generally, ROM stores operating routines, and RAM stores programmable parameters and variables.

Microprocessor 12 preferably also has an input/output port connected to a telemetry interface 26 via line 28. Stimulator 10, when implanted, is thus able to receive variable and control parameters from an external programmer and to send data to an external receiver if desired. As such, operating parameters stored within microprocessor 12 may be selectively altered non-invasively. Many suitable telemetry systems are known to those skilled in the art. U.S. Pat. No. 4,539,992 by Calfee, et al., issued Sep. 10, 1985 and entitled "Method and Apparatus for Communicating with Implanted Body Function Stimulator" describes an example of a telemetry system and encoding arrangement.

Control lines 30 and 32 connect microprocessor output ports to inputs of an atrial stimulus pulse generator 34 and a ventricular stimulus pulse generator 36, respectively. Pulse parameter data, such as amplitude, width, enable/disable, and pulse initiation codes transmit to generators 34 and 36 via lines 30 and 32, respectively. In addition, control lines 38 and 40 connect microprocessor input ports to outputs of an atrial sense amplifier 42 and a ventricular sense amplifier 44, respectively. Atrial sense amplifier 42 detects the occurrences of P-waves, and ventricular sense amplifier 44 detects the occurrences of R-waves.

The input of atrial sense amplifier 42 and the output of atrial stimulus pulse generator 34 connect to a first conductor 46 which connects to a first conventional type lead 48. An electrically conductive pacing/sensing tip 52 is located at a distal end of lead 48. This pacing/sensing tip electrically connects to conductor 46 and connects, for example, to heart 50 in right atrium 54.

The input of ventricular sense amplifier 44 and the output of ventricular stimulus pulse generator 36 connects to a second conductor 56 which connects to a second conventional type lead 58. An electrically conductive pacing/sensing tip 62 is located at a distal end of lead 58. This pacing/sensing tip electrically connects to conductor 56 and connects, for example, to heart 50 in right ventricle 60. Leads 48 and 58 may be inserted into heart 50 transvenously or in any other suitable manner.

Conductors 46 and 56 conduct the stimulus pulses generated in atrial and ventricular stimulus pulse generators 34 and 36, respectively, to pacing/sensing tips 52 and 62. Pacing/sensing tips 52 and 62 and corresponding conductors 46 and 56 also conduct sensed cardiac electrical signals in the heart to atrial and ventricular sense amplifiers 42 and 44.

Cardiac stimulator 10 also may serve as a defibrillator. In this regard, microprocessor 12 controls a high voltage defibrillator circuit 64. Two high voltage leads 66 and 68 connect to the heart with two electrodes 70 and 72. In the illustrated embodiment, epicardial patch electrodes are diagrammatically represented; although, other electrode configurations, such as endocardial electrodes or others known to those skilled in the art, may be used.

The input and output ports of microprocessor 12 also connect to various sensors 74 via a bidirectional control bus 76. Implantable cardiac stimulators often employ sensors or sensing capabilities. Sensors 74 may be a variety of different sensing devices which gather information about the patient. These sensors, for example, may sense ventilation, acceleration, activity, oxygen level, blood pressure, temperature, blood oxygenation, blood pH, impedance, adrenaline levels, or the like.

Those skilled in the art will recognize that the present invention may be used with various implantable devices, with stimulator 10 in FIG. 1 illustrating an example of one such device. Other possible implantable devices, for example, may be directed solely or jointly to tachycardias, bradycardias, or fibrillation, and, in this regard, comprise a defibrillator, a single or dual chamber pacer, or combinations thereof. In addition, the method of the invention may be used in devices which do not stimulate the heart at all or devices which are not implantable. Such devices, however, must be able to sense or record the cardiac wave-form in order to measure the beat-to-beat intervals of the heart. Measurement of this interval may be done remotely from the heart, for example with electrodes placed on the patient, or within the heart itself, for example, from either the atrium, ventricle, or both.

In order to obtain the beat-to-beat interval between successive heart beats, signals from the heart communicate from electrodes to the cardiac stimulator or other such monitoring device. In FIG. 1, either sensing tip 52 or sensing tip 62 detects the heart's signals. Once these signals are detected, they may be processed in various ways to acquire the beat-to-beat intervals. U.S. Pat. No. 5,201,321 by Fulton, issued Apr. 13, 1993, and entitled "Method and Apparatus for Diagnosing Vulnerability to Lethal Cardiac Arrhythmias" teaches a method and apparatus for receiving heart beat signals and then calculating the beat-to-beat intervals. As an example, the signal received from the heart is digitized, and the output is provided to a peak detector which is connected to a memory. The peak detector measures the timing of the peak amplitude, such as the A—A, P—P, V—V, or R—R interval of the heart signal (A—A interval is the time between successive atrial depolarizations as measured from within the atrium; P—P interval is the time between successive atrial depolarizations as measured on the body of the patient; V—V interval is the time between successive ventricular depolarizations as measured from within the ventricle; and R—R interval is the time between successive ventricular depolarizations as measured on the body of the patient). The memory or recording device then stores the timing of the successive intervals. The timing intervals usually are measured in units of time or in terms of the number of samples between beats. The particular method or apparatus used to record the beat-to-beat intervals is less critical, as long as these intervals are accurately obtained.

Preferably, the beat-to-beat intervals are recorded during predetermined lengths of time or epochs. The epoch period typically will endure for several minutes, for example five minutes, or for a given number of heart beats, for example 100 to 1000 beats. The length of the epoch is programmable and may vary. Preferably, beat-to-beat intervals are continuously recorded for successive epochs.

The overall operating method and algorithm of the present invention is illustrated in a discussion of the flow diagrams which follow. The flow diagrams represent the program structure under which microprocessor 12 preferably operates. The program structure may be written in a low level computer language, such as assembly, and retained in a memory within the microprocessor.

Figure 2:
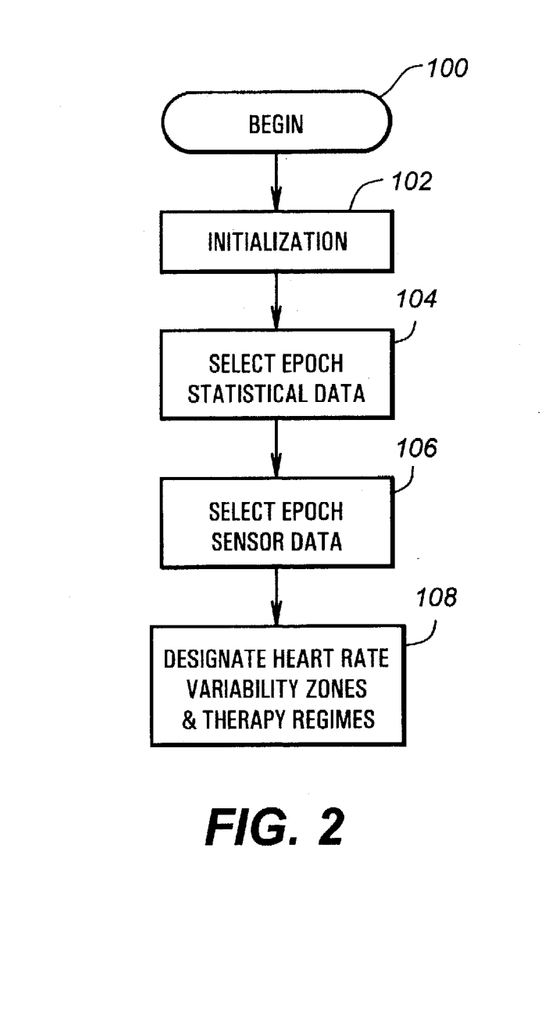
FIG. 2 is a flow diagram for specifying heart rate variability parameters.

Looking first to FIG. 2, a program structure commences at begin 100. As represented at block 102, conventional initialization procedures are performed. These procedures may include setting all pointers, registers, and counters, and clearing specified memory locations. Epoch statistical data then is selected, as depicted in block 104. This statistical data generally includes computational and statistical algorithms, variables, equations, and the like known to those of ordinary skill in the art. Typically, this statistical data will include any combination of at least one of a measure of central tendency or a measure of dispersion. Additional examples of statistical variables and equations which may be calculated for an epoch period include: mean, MAD (mean absolute deviation), median, mode (most commonly occurring heart rate variability interval), amplitude of mode (percentage that mode occurs), variation range (difference between highest and lowest heart rate variability interval), PNN50 (percentage of heart rate intervals having a duration longer than 50 ms), standard deviation, range, power spectral density, and variance.

In order to evaluate the heart rate variability of the patient and, in turn, forecast the patient's heart condition, sensing data may be used in addition to statistical data. Looking now to block 106, epoch sensor data is selected. Sensing data is derived from sensors or electrodes which measure physiological conditions of the patient. Such sensors may be directed toward sensing, for example: evoked QT intervals, respiration, stroke volume, central venous oxygen saturation, right ventricular pressure, blood pressure, muscle noise, acceleration, impedance, activity or motion, temperature, blood pH, and adrenaline. An activity sensor, for example, is capable of measuring the movement and motion of the patient.

Any combination of statistical equations/algorithms and sensing data may be utilized to evaluate heart rate variability. Statistical equations, for example, may be used singly or incorporated into a statistical algorithm to produce statistical data for a given epoch. This statistical data, in turn, may be combined with sensing data. Together, the statistical and sensing data form the epoch data for a given epoch.

Figure 3:
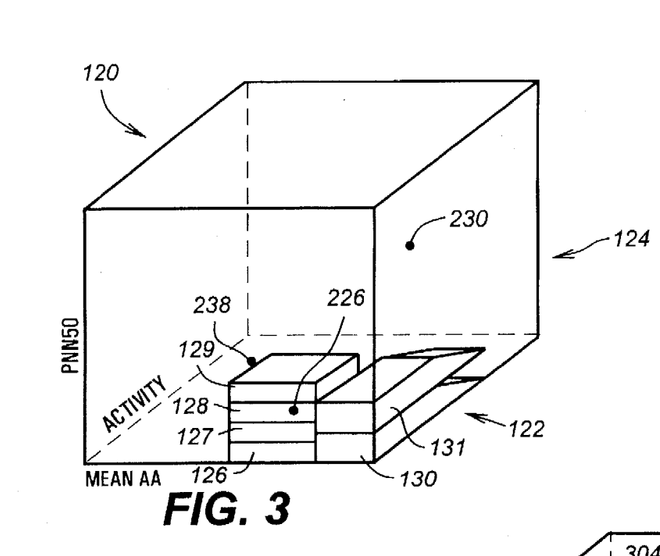
FIG. 3 is a perspective view of heart rate variability zones.

Block 108 shows that heart rate variability zones and corresponding therapy regimes are designated and then stored into memory. The heart rate variability zones define normal and abnormal heart rate variability for the patient. FIG. 3 illustrates an exemplary heart rate variability zone configuration generally at 120. Three separate axes define configuration 120. Mean value of AA intervals defines the x-axis; PNN50 defines the y-axis; and patient activity defines the z-axis. Within configuration 120, an abnormal heart rate variability zone is shown generally at 122. A normal heart rate variability zone 124 occurs outside the boundaries of abnormal zone 122.

A set of parameters defines the boundaries or limits of abnormal zone 122 and normal zone 124. These parameters include values or ranges of values for each of the three axes. Preferably, the parameters divide abnormal zone 122 into a plurality of heart rate variability sub zones. FIG. 3 shows abnormal zone 122 subdivided into six different subzones 126–131, respectively. Separate and independent sets of parameters define each subzone 126–131. Each of the subzones corresponds to a different heart rate variability state, and the subzones may have a hierarchical format with respect to the level of abnormality of heart rate variability or with respect to the corresponding cardiac condition of the patient. For example, subzone 126 may represent heart rate variability conditions with a more heightened degree of alert than subzone 129.

In FIG. 3, a somewhat rectangular configuration illustrates each subzone. It will be appreciated that these configurations are for illustrative purposes and will vary depending on the parameters which define the bounds of the subzones. In addition, the configurations generally will depend not only on the statistical and sensor data selected to define the subzones but also on particular physiological conditions and requirements of an individual patient. In this regard, each patient undergoing heart rate variability analysis may require a different set of parameters defining each subzone 126–131. Further yet, the subzones may have a plurality of different parameters. In FIG. 3, three different parameters define abnormal zone 122. The number of parameters may vary from one to more than four or five. A fourth parameter, for example, could be time of day. Configuration 120 depicts three parameters and six subzones for illustration.

The parameter's bounds or limits for each subzone may be established before heart rate variability analysis commences. For example, a doctor or clinician may assign specific numerical values for each of the subzones based on the medical history of a patient. Alternatively, the patient may undergo monitoring to determine limits for abnormal and normal heart rate variability. A Holter monitor or other device used to record and store heart rate variability data may monitor the heart rate variability of the patient. Thereafter, limits for each of the subzones may be calculated based on this data. As another alternative, the boundaries defining the subzones may be based on an initial estimation and pre-programmed into memory.

Each subzone also has an associated therapy regime. The therapy regimes preferably have a hierarchical format with respect to the level of abnormality of heart rate variability or with respect to the corresponding cardiac condition of the patient. In this regard, a lesser degree of aggressiveness may be associated with a subzone having a more acceptable heart rate variability and a more aggressive therapy assigned to a subzone having more abnormal heart rate variability.

Figure 4:
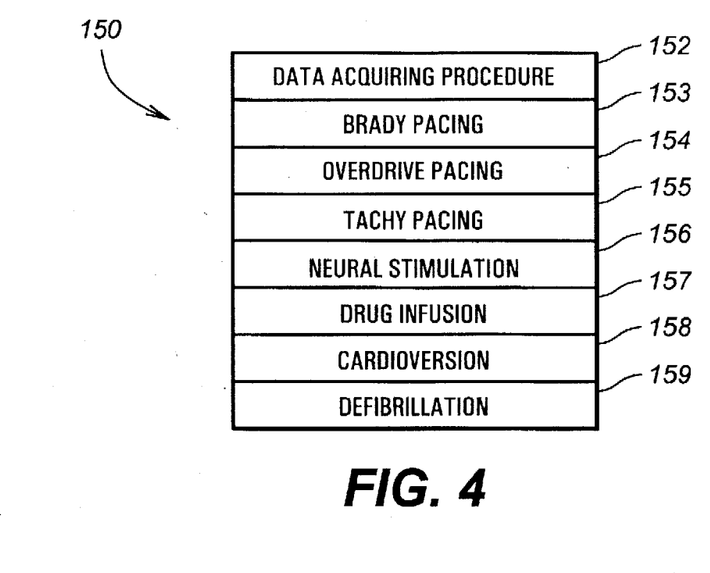
FIG. 4 is a block diagram of a therapy regime.

FIG. 4 illustrates an exemplary therapy regime generally at 150. In this figure, therapy regime 150 has eight different therapy levels 152–159. Commencing then with the least aggressive regime, therapy level 152 calls for the initiation of more energy expensive tests or data acquiring procedures to better or more accurately assess the heart condition of the patient. These procedures may include various forms of added vigilance, such as activating a sensor which senses ventilation, acceleration, impedance, activity or motion, oxygen, blood pressure, temperature, blood oxygenation, blood pH, or adrenaline. Further, the procedures may include increasing the level of diagnostic data collection, for example, waveform storage with increased sampling rate, increasing diagnostic biopotential channel bandwidth, increasing parameter recordings, and increasing signal processing. Further yet, additional statistical data may be calculated or additional statistical algorithms employed. This statistical data may be based on heart rate intervals stored during current or previous epochs. Additionally, the initiation of completely non-invasive procedures are possible. For example, a warning or alarm may communicate to the patient, health provider, clinician, or a designated location. Such a warning, for example, could communicate the patient's pending heart condition or, alternatively, alert a clinician of the patient's condition or need for added attentiveness. Next, therapy level 153 calls for bradycardia pacing or antibradycardia pacing. If the heart rate variability were more abnormal, a higher rate overdrive pacing would be implemented, as shown in therapy level 154. Level 155 illustrates antitachycardia pacing and would occur, for example, if the patient were experiencing atrial flutter or ventricular tachycardia. The next higher level 156 calls for a form of neural stimulation to stimulate vagal activity of the patient. Level 157 illustrates activation of a counteractive drug dose. A drug infusion pump could infuse drugs to the patient to counteract any increased adrenalin and act as a tranquilizer. As such, the drug would effectively normalize heart rate variability. If the patient experiences yet a more extreme cardiac condition, a cardioversion shock may be initiated, as shown at level 158. An extreme level 159 calls for administering a defibrillation shock if the patient exhibits even more extreme cardiac conditions or exhibits extreme abnormal heart rate variability.

Selective activation of therapy regime 150 saves energy and thus conserves power supply longevity. In this regard, a heightened degree of vigilance generally is not initiated until the patient exhibits an abnormal heart rate variability. Once abnormal variability is detected, a therapy regime, such as shown in levels 152–159, is initiated. Possible regimes, as noted, include additional sensing, computing, or the like. Since these regimes require power to initiate, selective activation saves energy. Further, during periods of abnormal heart rate variability, non-essential computational and diagnostic activity occurring within the stimulator may be suspended, halted, or not commenced in order to reduce potential sources of interference and devote computational resources to monitoring and diagnosing heart rate variability or a cardiac event. For example, if an abnormal heart rate variability is detected, unnecessary reforming of a defibrillator capacitor may be stopped.

Each therapy level 152–159 may correspond to a different heart rate variability subzone. For example, looking also to FIG. 3, subzone 126 may correspond with therapy level 152, while subzone 131 corresponds with therapy level 159. It will be appreciated that FIG. 4 illustrates an example of one therapy regime. However, alternative therapy regimes may differ for individual patients and be tailored to meet specific cardiac requirements.

Additionally, other types of heart rate measurement and evaluation schemes also are available. For example, time domain analysis or a frequency domain analysis are two common ways researchers use to examine heart rate variability. In the time domain analysis, a graph typically displays the R—R intervals as the number of beats occurring during a specified time. As an example, ECG monitors may record and calculate heart rate variability. In the frequency domain analysis, a Fourier transform algorithm decomposes sequential R—R intervals into a sum of sinusoidal functions. A graph typically displays the result of this algorithm and shows the amplitude of the patient's heart rate fluctuations at different oscillation frequencies. The frequency domain analysis is particularly advantageous in some instances because certain frequency bands within the spectral analysis are associated with autonomic nervous system control of sinus node period. See J. Thomas Bigger, et. al, "Frequency Domain Measures of Heart Period Variability and Mortality After Myocardial Infarction" *Circulation*, Vol. 85 (1992), pp. 164–171.

Figure 5:
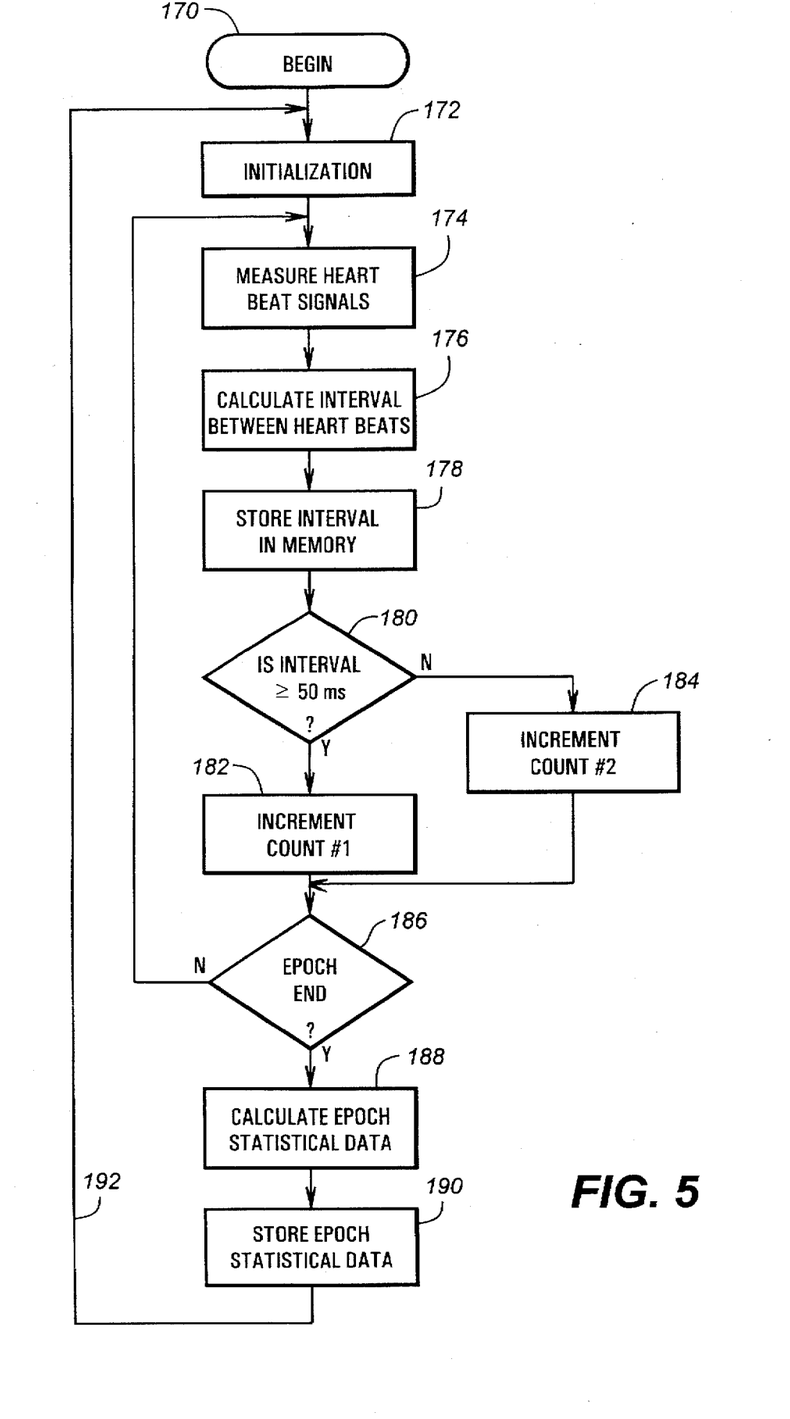
FIG. 5 is a flow diagram for calculating epoch statistical data.

Looking now to FIG. 5, a program structure is shown for calculating selected epoch statistical data. The program structure begins at 170 and commences conventional initialization procedures at 172. Next, as shown in block 174, measurement of successive heart beat signals occurs. Then, as represented at 176, the beat-to-beat intervals between heart beats of the patient is calculated. These intervals represent the time period between successive beats. A memory stores the intervals, as shown in block 178. Next, a query is made at block 180 to determine whether the beat-to-beat interval has a length of time greater or less than 50 ms. If the beat-to-beat interval is greater than or equal to 50 ms, then a counter is incremented at 182. If the interval is less than 50 ms, a counter is incremented at 184. The counters may be in the microprocessor or control circuitry and count the number of times during a single epoch the beat-to-beat intervals are greater or less than 50 ms. At block 186, a query determines if the epoch period ended. If the epoch period has not ended, then the program structure returns to block 174 and continues to measure intervals between successive heart beats. If the epoch has ended, statistical data is calculated for the epoch, as shown at 188. The statistical data calculated at 188 is calculated for the data collected during the epoch. As illustrated in FIG. 3, the statistical data may also include, for example, PNN50 and Mean. Once the statistical data is calculated, it is stored into memory, as shown in block 190. In addition to storing the statistical data for the current epoch, counts one and two, the timing of the intervals, and the time of day also are stored. The program structure of FIG. 5 repeats, as shown along line 192, and again begins to measure heart beat intervals and calculate statistical data for succeeding epoch periods.

Figure 6:
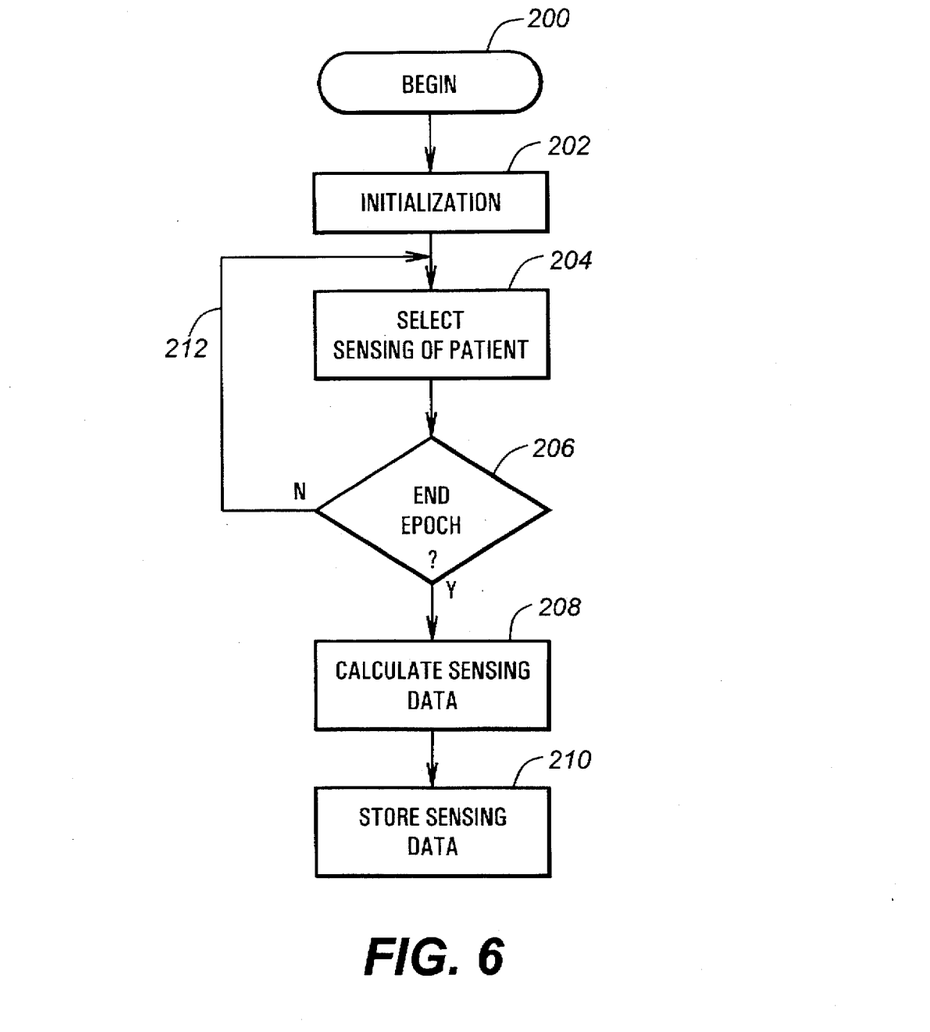
FIG. 6 is a flow diagram for calculating epoch sensing data.

Turning now to FIG. 6, a program structure commences selected sensing of the patient and calculation of sensing data. The program structure begins at 200 and initiates conventional initialization procedures at 202. Next, as shown in block 204, selected sensors are initiated and begin to collect information for the current epoch period. As noted, a variety of different sensing devices may sense and collect data from the patient. FIG. 3 illustrates initiation of an acceleration, activity, or motion sensor. Next, a query is made at block 206 to determine whether the epoch period has ended. If the epoch period has not ended, then the program structure returns to block 204 and continues to collect information. If the epoch has ended, the program structure proceeds to block 208, and the sensors selected in block 204 calculate sensing data for the epoch. For example, activity signals received during the epoch may be averaged to indicate a mean activity rate As shown in block 210, memory stores the sensing data and the time of day. At the end of the epoch, the program structure of FIG. 6 repeats, as shown along line 212, and again begins to sense using the selected sensors.

Figure 7:
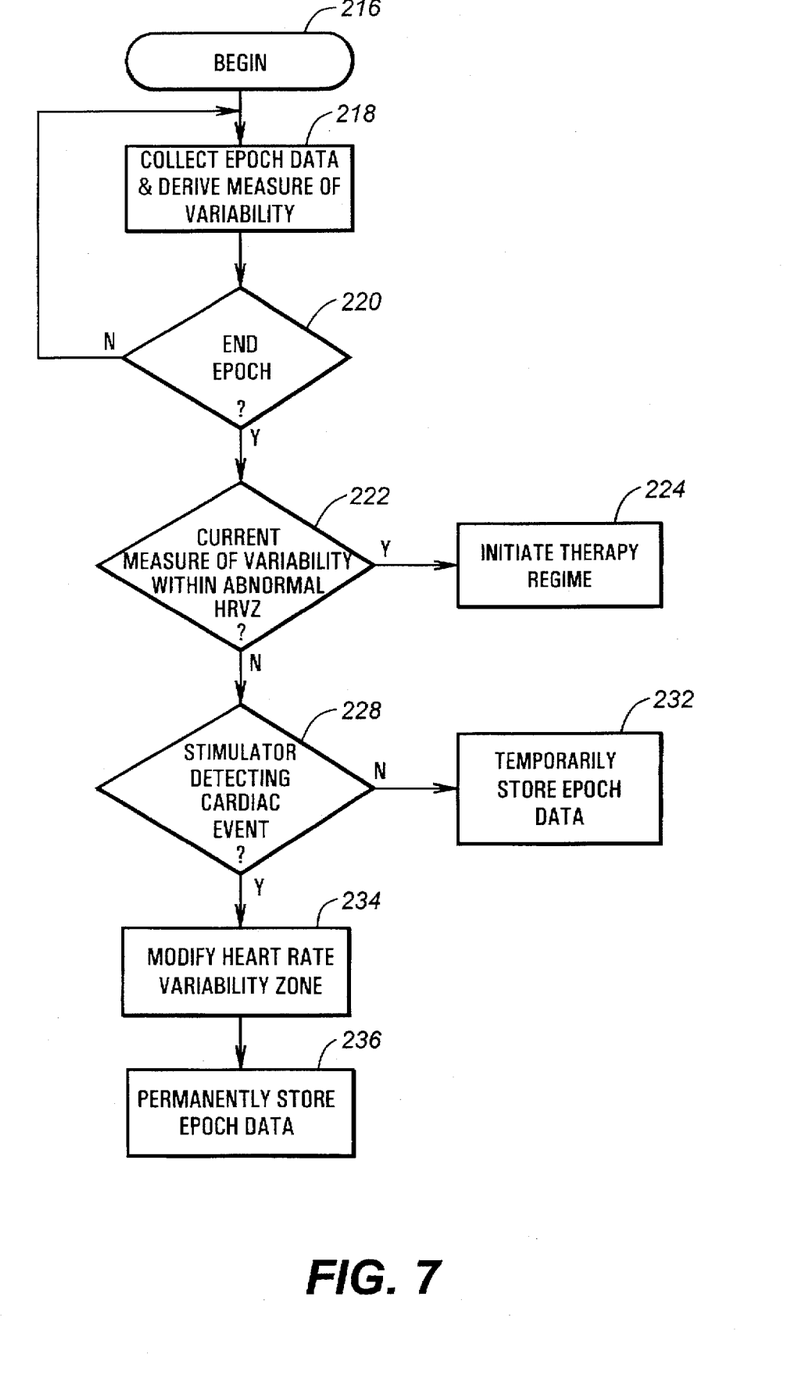
FIG. 7 is a flow diagram for comparing epoch data with stored heart rate variability parameters.

Looking now to FIG. 7, a program structure is shown for modifying stored heart rate variability zones which were previously stored into memory. The heart rate variability zones are automatically customized to adapt to an individual person's physiological and cardiological conditions. The program structure begins at 216 and then proceeds to block 218 which specifies collecting epoch data and deriving a measurement of heart rate variability. Epoch data, including sensing and statistical data, is collected and calculated as described in connection with FIGS. 2, 5, and 6. The measurement of heart rate variability is derived from the epoch data. This measurement of variability represents a measure of the person's or subject's heart rate variability for a given epoch period and includes all of the epoch data or selected portions. Next, a query in block 220 is made as to whether the end of the epoch period is reached. If the answer is negative, then epoch data is continued to be collected. If the answer is affirmative, the program structure continues to block 222 and a query is made whether present measurement of heart rate variability is within an abnormal heart rate variability zone. FIG. 3 illustrates this occurrence. As shown, three different axes (mean AA, PNN50, and activity) define abnormal heart rate variability zone 122 and normal heart rate variability zone 124. The measurement of heart rate variability is compared with zones 122 and 124 to determine the present cardiac condition and heart rate variability of the patient for the present epoch.

If the present measurement of heart rate variability is within abnormal heart rate variability zone 122, then, as shown in block 224, corresponding therapy is initiated. For example, FIG. 3 shows a possible location 226 within subzone 128. If, on the other hand, the present measurement of heart rate variability is not within abnormal heart rate variability zone 122, then the query of block 228 is presented. FIG. 3 shows a possible location 230 within normal zone 124 and outside the bounds of abnormal zone 122.

Block 228 queries whether the stimulator or measuring device is detecting any form of abnormal cardiac condition. For example the stimulator may be initiating a therapy, detecting a cardiac event, or within a heightened alarm, warning, or sensing condition. For example, the patient may be experiencing a degree of tachycardia, bradycardia, fibrillation, dysrhythmia, arrhythmia, or the like. If the answer to block 228 is negative, then the program structure proceeds to block 232 and the epoch data, including the measurement of heart rate variability, is temporarily saved into memory. If, however, the answer to block 228 is an affirmative, then heart rate variability zone configuration 120 of FIG. 3 is modified to include the measurement of heart rate variability corresponding to the present epoch sensor and statistical data. Modification, for example, may include enlarging or shortening the boundaries of one or more of subzones 129–131. Memory then stores the epoch data and measurement of heart rate variability as shown in block 236.

Figure 8:
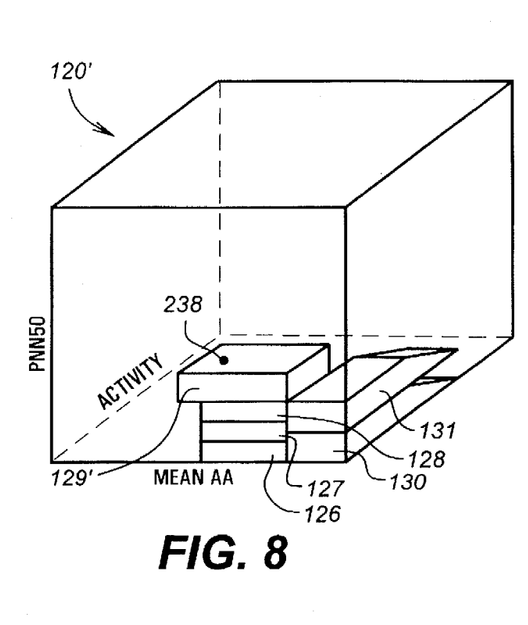
FIG. 8 is a perspective view of modified heart rate variability zones.

FIG. 3 illustrates a possible location 238 which is not initially within abnormal zone 122. Thus, no therapy would be initiated due to heart rate variability data of the patient. However, if the stimulator or measuring device concurrently detects an abnormal cardiac condition, the stimulator itself may initiate a therapy or heightened level of vigilance. In this instance, the parameters of abnormal zone 122 change to include the parameters of location 238. FIG. 8 illustrates this occurrence wherein the parameters of subzone 129 enlarge to include location 238. The modified heart rate variability zone configuration 120', including modified subzone 129', is permanently stored into memory. Subsequent measurements of heart rate variability are then compared to modified configuration 120'.

Figure 9:
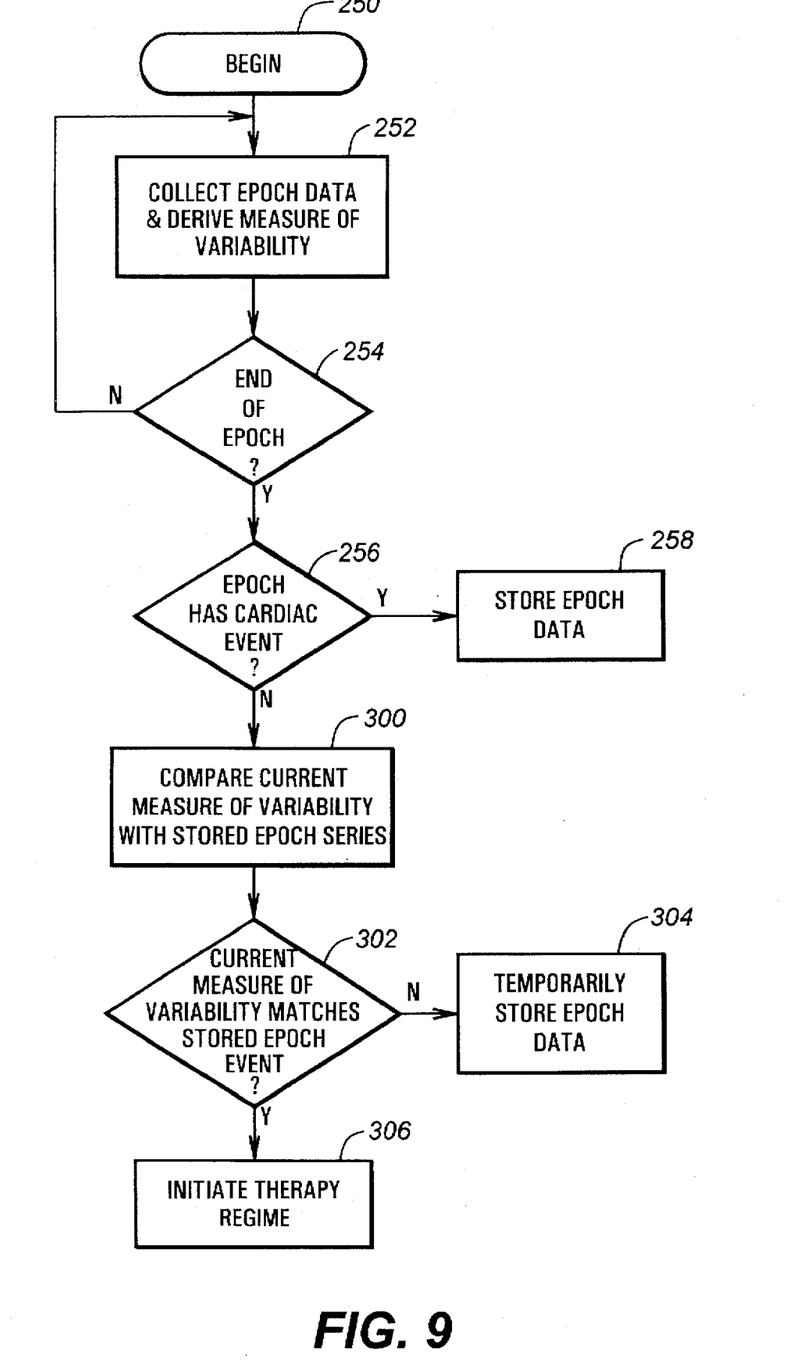
FIG. 9 is a flow diagram for comparing current epoch data with stored epoch data.

Looking now to FIG. 9, a program structure is shown for comparing present epoch data with previously stored epoch data to determine the heart condition of the patient. The previously stored epoch data represents instances in which the patient experienced a cardiac event or some form of abnormal cardiac condition. A comparison between the present epoch data and the stored epoch data then aids in predicting a re-occurrence of the event.

The occurrence of a cardiac event signifies that the patient's heart is experiencing a cardiac anomaly. Such an anomaly, for instance, may be recognized as an abnormal cardiac rhythm, as a cardiac complication, or as an indication of a possible impending abnormal cardiac condition. Examples of an anomaly would include arrhythmia, dysrhythmia, fibrillation, tachycardia, bradycardia, flutter, myocardial infarction, heart disease or sickness, or the like.

Figure 10:
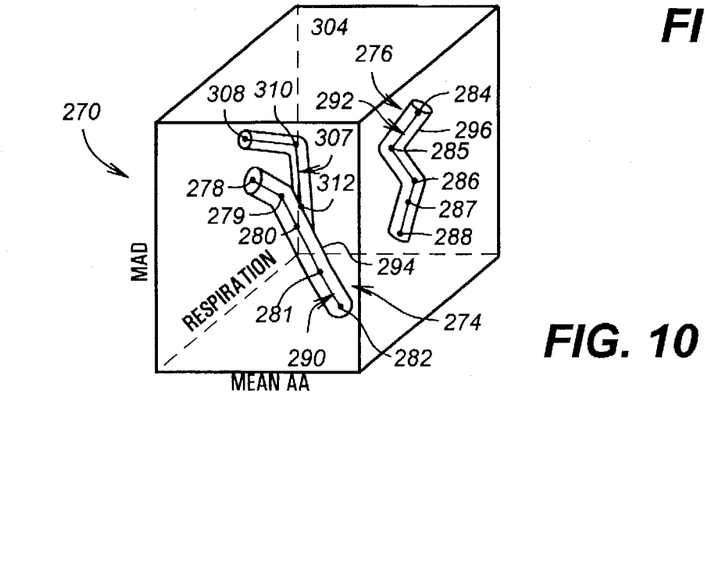
FIG. 10 is a perspective view of a series of epoch data locations leading to a cardiac event.

The program structure begins at 250 and then proceeds to block 252 which specifies collecting epoch data and deriving a measurement of heart rate variability. FIGS. 2, 5, and 6 describe the collection and calculation of epoch data. Next, a query in block 254 is made as to whether the end of the epoch period is reached. If the answer is negative, then the program structure loops to block 252, and epoch data is continued to be collected. If the answer is affirmative, the program structure continues to block 256 and a query is made as to whether a cardiac event has occurred. If a cardiac event occurs, memory stores the epoch data as shown in block 258. FIG. 10 illustrates storage of this epoch data.

FIG. 10 shows an exemplary heart rate variability zone configuration 270 having mean AA value as the x-axis, MAD as the y-axis, and patient respiration as the z-axis. Two hypothetical epoch series are shown at 274 and 276, respectively. Epoch series 274 includes a plurality of measurements of heart rate variability shown at 278–282. Measurements 278–282 represent epoch data locations leading to a cardiac event shown at measurement 282. Epoch series 276 illustrates a plurality of measurements of heart rate variability 284–288 leading up to a cardiac event represented at location 288. Each of the measurements includes all or part of the epoch data and other information collected and stored during a corresponding epoch. Epoch series 274, for example, may have ended in a bradycardia event at location 282. Pathway 290 represents an abnormal heart rate variability path or zone and is shown as a line leading to measurement 282. Epoch series 276 may have ended in a tachycardia event at measurement 288. A pathway 292 is shown as a line leading to this measurement.

Each heart rate variability pathway 290 and 292 may be expanded to include an abnormal heart rate tolerance zone, shown at 294 and 296, respectively. Tolerance zones 294 and 296 serve to enlarge pathways 290 and 292 and provide broader limits or boundaries defining the epoch series leading to the cardiac event. Preferably, the tolerance zone would expand pathways 290 and 292 from about 10% to 20%.

Epoch series 274 and 276 may provide a predictable avenue through which subsequent cardiac events occur. In this regard, individual patients may experience numerous cardiac events over a given period of time. Two or more of these events may have a preferred or common pathway leading to a particular event. For example, two separate cardiac events may start at different measurement locations but progress to or through a zone of commonality. The pathways, in fact, may partially or fully overlap. As such, the stored pathways may be compared with present pathways to aid in forecasting future cardiac events or to aid in recognizing the onset of a current event.

Additionally, cardiac events occur suddenly or develop over a more extended period of time. Once an event occurs, the present epoch data exhibiting that event is stored in permanent memory. In addition, prior epoch data also is permanently stored into memory. Thus, memory stores a series of epoch data once a cardiac event occurs. The amount and number of prior epoch data stored may depend on memory allocation availability, on the length of epoch time, or on the compressibility of the data, for example. Preferably, about several hours of prior epoch data are stored after the occurrence of a cardiac event.

The time of day in which the epoch occurs also may be a factor when comparing a current epoch with a stored epoch series. Epoch data may exhibit a circadian variation over a given time period. For example, when a person is sleeping, the mean heart rate, mean minute ventilation (i.e., an indication of the metabolic demand), and mean activity will be lower, and PNN50 and mean absolute deviation will be relatively higher. When the person is awake and active, such as exercising, the mean heart rate, mean minute ventilation, and mean activity will be relatively higher, and the PNN50 and mean absolute deviation will be relatively lower.

As another factor, a smaller amount of variability exists at higher heart rates. For example, a person with a heart rate of 100 bpm typically will have more sympathetic nerve activity inhibiting vagal action. In this situation, the heart rate variability of the patient expectedly is extremely low. If the heart rate were maintained at 100 bpm and pacing used to effectuate heart rate variability, little effect may result.

Turning back now to FIG. 9, as noted, if the answer to the query in block 256 is positive, then the epoch data is permanently stored into memory, as shown in block 258 and described in connection with FIG. 10. If the answer is negative, then a comparison is made between the current measurement of heart rate variability and stored epoch series, as shown in block 300. Block 302 then queries whether the current measurement of heart rate variability matches the stored epoch series. If no match exists, then the epoch data is temporarily stored, as shown in block 304. If a match does exist, then block 306 indicates an appropriate therapy is initiated.

FIG. 10 illustrates the comparison between current measurement of heart rate variability and stored epoch series. Epoch series 307 has three measurements of heart rate variability 308, 310, and 312. Two measurements or locations 308 and 310 are shown outside the boundaries or limits of either pathway 290 and tolerance zone 294 or pathway 292 and tolerance zone 296. Thus, neither of these two measurements match the stored epoch series. However, measurement 312 is within the boundaries of tolerance zone 294. Thus, a match exists between measurement 312 and epoch series 274.

Any of a variety of therapy regimes may be initiated if the current measurement of heart rate variability matches the stored epoch series. FIG. 4 shows alternate therapies. As one possibility, the same therapy regime originally initiated during the occurrence of the stored epoch series also could be initiated. For example, since measurement 304 in FIG. 10 is within the boundaries of tolerance zone 294, the same therapy initiated with measurement 279 or 278 could be initiated. Therapy regimes with a conservative and less aggressive approach also are possible. In this instance, more energy expensive vigilance may suffice. For example, additional sensors may be activated or a warning or alarm may be communicated. Alternatively, the aggressiveness of a therapy regime may depend on the potentially ensuing event. For example, pathway 274 may have led to a slow ventricular tachycardia which was otherwise not fatal to the patient. Antitachycardia pacing may have sufficed to correct the arrhythmic event. A similar therapy regime could be employed.

Since certain changes may be made in the above-described apparatus and method without departing from the scope of the invention herein involved, all matter contained in the description or shown in the accompanying drawings shall be interpreted as illustrative and not in a limiting sense.

What is claimed:

1. A medical device, comprising:

an electrode for detecting a series of heart beat signals from the heart of a patient;

means for providing a therapy regime to a heart of a patient;

memory having stored therein at least one heart rate variability zone with a corresponding therapy regime; and control circuitry in electrical communication with said electrode, said control circuitry having means for receiving said series of heart beat signals and for computing a measurement of heart rate variability, means for comparing said measurement of heart rate variability to said heart rate variability zone, means for initiating said therapy regime if said heart rate variability zone includes said measurement of heart rate variability, means for modifying said heart rate variability zone if said heart rate variability zone does not include said measurement of heart rate variability and said control circuitry detects a cardiac anomaly, and means for storing said modified heart rate variability zone in said memory.

2. The medical device of claim 1 in which said heart rate variability zone is an abnormal heart rate variability zone and said medical device further comprises means for predicting a cardiac anomaly when said measurement of heart rate variability falls within said abnormal heart rate variability zone.

3. The medical device of claim 1 in which:

said heart rate variability zone includes an abnormal zone defining abnormal heart rate variability and a normal zone defining normal heart rate variability; and further comprising means for disabling selected computational and diagnostic activities occurring within said control circuitry while said measurement of heart rate variability is within said normal zone.

4. The medical device of claim 1 in which said means for initiating said therapy regime includes at least one of a sensor, a stimulus generator, a defibrillator, neural stimulation, or drug infusion.

5. The medical device of claim 1 in which:

said heart rate variability zone includes an abnormal zone defining abnormal heart rate variability conditions for the heart of said patient and a normal zone defining normal heart rate variability conditions for the heart of said patient; and said means for initiating therapy includes means for initiating said therapy if said measurement of heart rate variability occurs within said abnormal zone.

* * * * *